US00PP08888P

United States Patent [19]

Danziger

[11] Patent Number: Plant 8,888

[45] Date of Patent: Sep. 13, 1994

[54] PETUNIA PLANT NAMED CAS 56

[75] Inventor: Gabriel Danziger, Post Beit Dagan, Israel

[73] Assignee: Florfis AG, Binningen, Switzerland

[21] Appl. No.: 162,695

[22] Filed: Dec. 7, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Foley & Lardner

[57] ABSTRACT

A new and distinct cultivar of petunia plant named Cas 56, characterized by the combined features of medium to large white flowers, light throat with dark violet veins, vigorous, bushy growth habit, semi-erect to overhanging plant habit, and light to medium green foliage.

2 Drawing Sheets

The present invention comprises a new and distinct cultivar of petunia, hereinafter referred to by the cultivar name Cas 56.

Cas 56 was originated from a hybridization made by the inventor Gabriel Danziger in a controlled breeding program in Moshav Mishmar Hashiva, Israel in 1992. The female parent was a seedling designated X 31. The male parent of Cas 56 was a seedling designated Y 43. Both parents are proprietary cultivars used in the breeding program.

Cas 56 was discovered and selected as one flowering plant within the progeny of the stated cross by Gabriel Danziger in 1992 in a controlled environment in Moshav Mishmar Hashiva, Israel.

The first act of asexual reproduction of Cas 56 was accomplished when vegetative cuttings were taken from the initial selection in December 1992 in a controlled environment in Moshav Mishmar Hashiva, Israel, by, or under the supervision of, Gabriel Danziger.

Horticultural examination of selected units initiated in December 1992 and continuing thereafter has demonstrated that the combination of characteristics are herein disclosed for Cas 56 are firmly fixed and are retained through successive generations of asexual reproduction.

Cas 56 has not been observed under all possible environmental conditions. The phenotype may vary significantly with variations in environment such as temperature, light intensity and day length without, however, any variations in genotype.

The following observations, measurements, and comparisons describe plants grown in Hillscheid, Germany, under greenhouse conditions which approximate those generally used in commercial practice.

The following traits have been repeatedly observed and are determined to be basic characteristics of Cas 56, which in combination distinguish this petunia as a new and distinct cultivar:

1. Medium to large white flowers.
2. Light throat with dark violet veins.
3. Vigorous, bushy growth habit, with branches fully extending in all directions from center of plant.
4. Plant habit semi-erect in the beginning, hanging as the plant matures.
5. Light to medium green foliage.

The accompanying photographic drawings show typical flower and foliage characteristics of Cas 56, with colors being as true as possible with illustration of this type. The photograph on Sheet 1 illustrates Cas 56 cultivated in a hanging basket. The photo on Sheet 2 comprises an enlarged showing of single flowers of the new cultivar.

In the following description, color references are made to The Royal Horticultural Society Color Chart. The color values were determined indoors in August. Flowers were taken from plants cultivated in hanging baskets in an open greenhouse in Hillscheid, Germany. For the description, the upper parts of the plants were observed or measured.

Classification:

*Botanical.*—A hybrid of the genus Petunia.

*Commercial.*—Petunia cv Cas 56.

INFLORESCENCE

Plant:

*Growth habit.*—Vigorous, branches initially semi-erect, later overhanging.

*Plant length.* 90–95 cm, measured from the base of the stems in the middle of the hanging basket to the tips of the hanging branches (28 week old plants).

*Blooming period.*—Comparatively late, begins 11 weeks after propagation of unrooted cuttings, continually flowering thereafter.

Stem:

*Thickness.*—Young branches, 2.5–3.0 mm; older branches 4–5 mm.

*Color.*—Light green, between 137 D and 143 C.

*Pubescence.*—Present.

*Branching.*—8 branches per week.

*Length of internode.*—25–30 mm.

Leaf:

*Arrangement of stem: Opposite, arranged decussately on stem.*

*Shape: Narrow/ovate.*

*Size (average)*: 65 mm long, 32 mm wide, based on largest leaves from a young stem of a plant in flower.

*Thickness: Medium.*

*Color.*—Light to medium green, 137 C.

*Pubescence.*—Present, very weak.

Flower:

*Orientation at opening.*—The bud and peduncle form an acute angle with the stem; the open flower and peduncle are oriented approximately at right angles to the stem.

*Type.*—Single

*Shape.*—Not completely round, slightly undulated margin.

*Diameter.*—75–85 mm.

*Color.*—Upper (inner) surface at opening: 155 A. Under (outer) surface at opening: 155 A. Upper (inner) surface at pollen maturity: 155 D. Under (outer) surface at pollen maturity: 155 D. Throat (inner surface): White to light green, with dark violet veining.

*Peduncle length.*—12–18 mm.

*Peduncle color.*—Medium green with some of anthocyanin near the base of the flower.

Reproductive organs.—Pistil: 1, green. Stamens: 5, fertile. Anther: Light-blue, with comparatively intense blue pollen. Filament: White.

Resistance: Very good resistance to rain and good heat tolerance.

It is claimed:

1. A new and distinct cultivar of petunia plant named Cas 56, as illustrated and described.

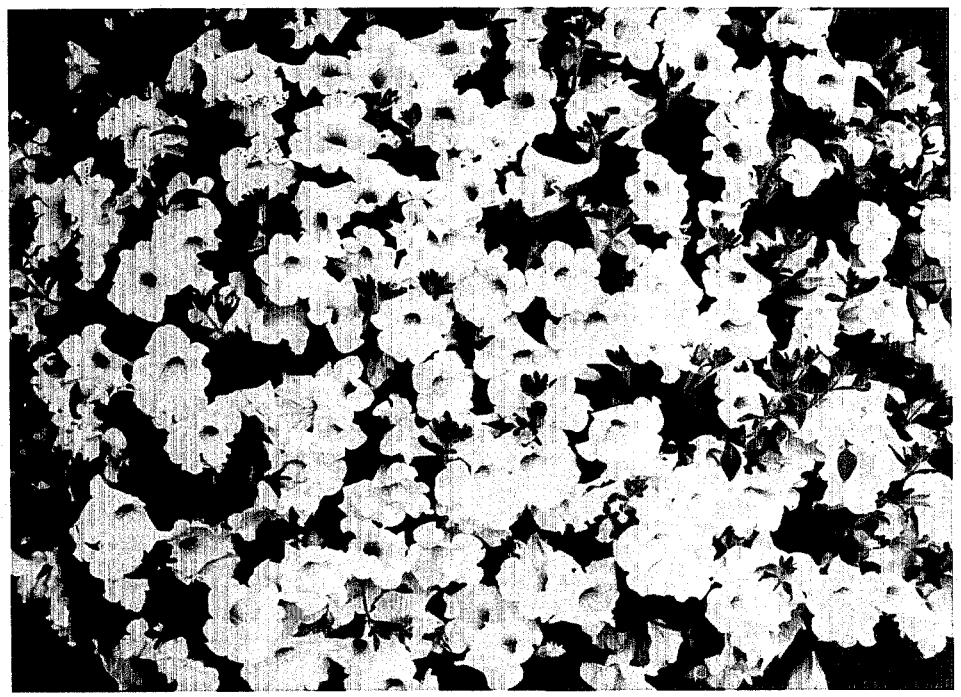

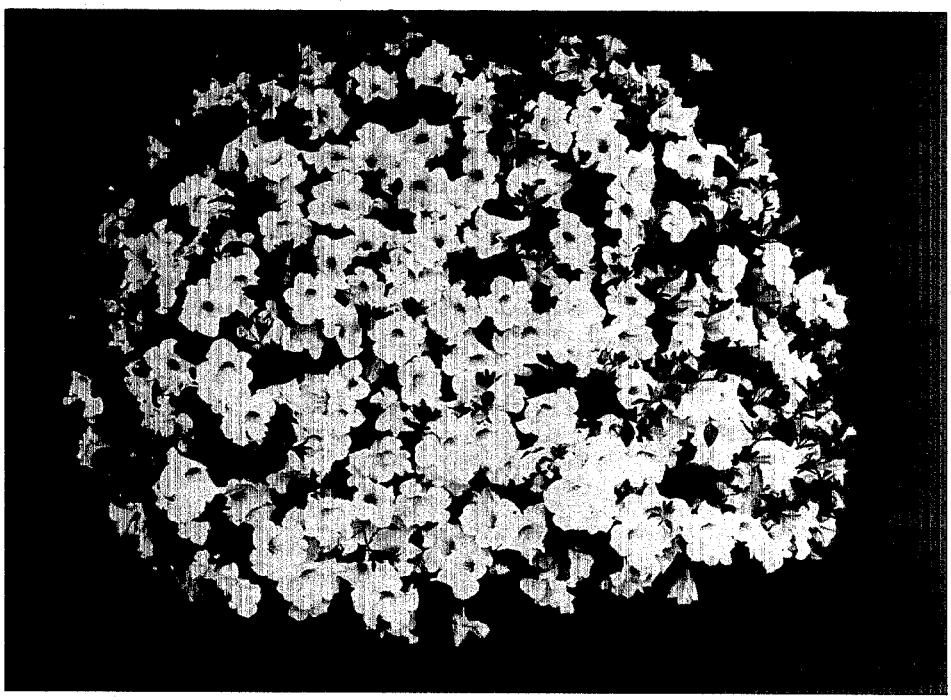

* * * * *